US006925881B1

(12) United States Patent
Kwun et al.

(10) Patent No.: US 6,925,881 B1
(45) Date of Patent: Aug. 9, 2005

(54) TIME SHIFT DATA ANALYSIS FOR LONG-RANGE GUIDED WAVE INSPECTION

(75) Inventors: Hegeon Kwun, San Antonio, TX (US); Sang-Young Kim, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 10/051,898

(22) Filed: Jan. 17, 2002

(51) Int. Cl.[7] ............................................. G01N 29/10
(52) U.S. Cl. ........................... 73/600; 73/598; 73/602; 73/622; 73/643
(58) Field of Search .................. 73/592, 597–600, 73/622, 623, 40.5 A, 602, 643

(56) References Cited

U.S. PATENT DOCUMENTS

| | | | |
|---|---|---|---|
| 4,001,693 A | 1/1977 | Stackhouse et al. | 364/421 |
| 4,083,229 A * | 4/1978 | Anway | 73/592 |
| 4,858,462 A * | 8/1989 | Coulter et al. | 73/592 |
| 4,885,711 A | 12/1989 | Neff | 364/574 |
| 5,315,538 A | 5/1994 | Borrell et al. | 364/574 |
| 5,456,113 A | 10/1995 | Kwun et al. | 73/587 |
| 5,457,994 A | 10/1995 | Kwun et al. | 73/587 |
| 5,499,190 A | 3/1996 | Takahashi et al. | 364/481 |
| 5,581,037 A | 12/1996 | Kwun et al. | 73/623 |
| 5,591,912 A * | 1/1997 | Spisak et al. | 73/623 |
| 5,767,766 A | 6/1998 | Kwun | 340/436 |
| 5,821,430 A | 10/1998 | Kwun et al. | 73/862.41 |
| 5,924,052 A | 7/1999 | Palm | 702/71 |
| 5,965,818 A | 10/1999 | Wang | 73/598 |
| 5,973,532 A | 10/1999 | Schmidt | 327/231 |
| 6,065,348 A * | 5/2000 | Burnett | 73/600 |
| 6,092,421 A | 7/2000 | Bar-Cohen et al. | 73/624 |
| 6,095,980 A | 8/2000 | Burns et al. | 600/453 |
| 6,148,672 A | 11/2000 | Cawley et al. | 73/622 |
| 6,151,014 A | 11/2000 | Zloter et al. | 345/177 |
| 6,163,292 A | 12/2000 | Liedtke et al. | 342/22 |
| 6,178,387 B1 | 1/2001 | Wang | 702/66 |
| 6,182,018 B1 | 1/2001 | Tran et al. | 702/66 |
| 6,212,944 B1 | 4/2001 | Kwun et al. | 73/116 |
| 6,453,247 B1 * | 9/2002 | Hunaidi | 73/592 |
| 2001/0045129 A1 * | 11/2001 | Williams et al. | 73/592 |

FOREIGN PATENT DOCUMENTS

JP          04019558 A  *  1/1992  .......... G01N 29/06

* cited by examiner

Primary Examiner—Hezron Williams
Assistant Examiner—Nashmiya Fayyaz
(74) Attorney, Agent, or Firm—Baker Botts L.L.P.

(57) ABSTRACT

A method of analysis long range guided wave data reflected from defects and geometric features such as welds in a structure. The method involves acquiring two sets of data, and time shifting one set of data relative to the other. Data points that match in time after the shifting are considered to represent defects or geometric features in the structure. The result of the method is exclusion of false signal data and automation of data analysis.

22 Claims, 3 Drawing Sheets

TIME SHIFT DATA ANALYSIS FOR LONG-RANGE GUIDED WAVE INSPECTION

TECHNICAL FIELD OF THE INVENTION

This invention relates to non-destructive testing, and more particularly to the use of long-range guided waves for such testing.

BACKGROUND OF THE INVENTION

Nondestructive testing has proven to be an essential tool for assessing corrosion and erosion related damage in large equipment and structures. For long lengths of structure, such as pipes, tubes, steel cables, and plates, long range guided wave inspective has proved to be effective. Using long range guided wave techniques, a long length of structure can be inspected quickly and economically from a given probe location.

One example of a long range guided wave technique is an ultrasonic technique based on the use of Lamb waves. The guided waves are generated by using piezoelectric probes and mechanically coupled into the material under inspection. The Lamb waves propagate between two parallel surfaces and can be used to detect changes in wall thickness. This technique is described in U.S. Pat. No. 6,148,672, to Cawley, Alleyne and Chan, entitled "Inspection of Pipes," assigned to Imperial College of Science, Technology of Medicine (London).

Another example of a long range guided wave technique uses magnetostrictive probes. These probes generate and detect mechanical waves in ferromagnetic material. Testing of a pipe involves two sets of an inductive coil encircling the pipe and a bias magnet. A time-varying magnetic field is applied to the pipe by the transmitting coil and this generates an elastic wave in the pipe due to the magnetostrictive effect. The waves propagate along the pipe in both directions. The receiving magnetostrictive probe uses the other encircling coil to detect changes in magnetic induction in the pipe due to the inverse magnetostrictive effect when the waves pass through. The system does not require a couplant or direct contact. This technique is described in U.S. Pat. No. 5,581,037, entitled "Nondestructive Evaluation of Pipes and Tubes Using Magnetostrictive Sensors," to Kwun and Teller, assigned to Southwest Research Institute (San Antonio, Tex.).

Guided waves can exist in various modes, such as longitudinal, flexural, and torsional wave modes in pipe or tube, and symmetric and antisymmetric Lamb wave and shear horizontal wave modes in plate. In each wave mode, they can exist in different forms, with the forms referred to as "orders". Guided waves are also dispersive, and therefore, their velocity of propagation varies with wave frequency.

To simplify analysis of the detected signals, the probes for long range guided waves are often controlled to generate a single wave mode of a fixed order that is propagated in a given direction, and to detect the same wave mode traveling in the opposite direction after reflection from a defect or a normal geometric feature such as a weld.

In practice, the control of wave mode and directionality is imperfect. As a result, extraneous wave modes are generated and detected, and extraneous waves may be propagated in directions other than the intended direction. These extraneous signals can be confused with the desired reflected signals, leading to erroneous data interpretation. Because of the complexities of guided waves, as well as of geometric features in structures, proper analysis of acquired data is time consuming and requires extensive knowledge of guided wave properties and interactions with geometric features in the structure.

SUMMARY OF THE INVENTION

One aspect of the invention is a method of analyzing long range guided wave data to identify signals of the intended wave made of a fixed order that are reflected from defects and geometric features in the intended direction. Two sets of reflection signals are acquired. The first data set is acquired from a first probe position. The second data set is acquired from a second probe position having a known separation from the first probe position. Signals whose amplitude exceed a pre-determined threshold value are then identified from both sets of data. Next, the signals in one set of data values are time-shifted by an amount that would cause the signals to occur at the same time if the probes were in the same position. The shifted data values are compared to the unshifted data values to determine any coincidence in time between two signals. Signals that coincide are interpreted as representing the correct signals that are reflected from defects and geometric features in the intended direction. Signals that do not coincide are interpreted as representing extraneous signals.

An advantage of the invention is that it provides simple and accurate data analysis of long range guided waves. The method identifies primary wave mode signals and excludes extraneous signals. The analysis is automated in a manner that permits the data to be interpreted quickly without requiring a high level of knowledge of the guided waves.

DETAILED DESCRIPTION OF THE INVENTION

Figure 1:
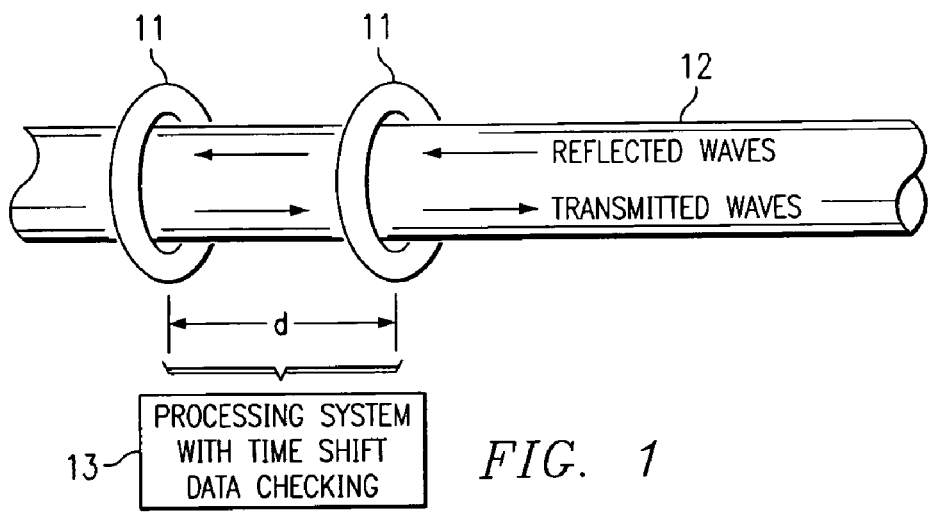
FIG. 1 illustrates a system for time-shift checking of guided wave data in accordance with the invention.

FIG. 1 illustrates a system 10 for analyzing guided wave data in accordance with the invention.

The reflected signals are detected from two probe positions 11 separated by a short distance. As discussed in the Background, there are various approaches to long range guided wave testing, and various types of probes may be used for such testing. Examples of suitable probes are those used for Lamb wave inspection or those used for magnetostrictive testing. In the example of FIG. 1, the probe at each position is of a type appropriate for magnetostrictive testing and encircles pipe 12. A suitable separation distance, d, between probe positions 11 is four inches.

The probe outputs are delivered to a processing system 13, which has memory and processing components suitable for implementing the method described herein. Processing system 13 is programmed with instructions for carrying out the algorithms described below, and may further be programmed with a suitable user interface for receiving operation commands and displaying results to an operator.

Time Domain Data Analysis

Figure 2:
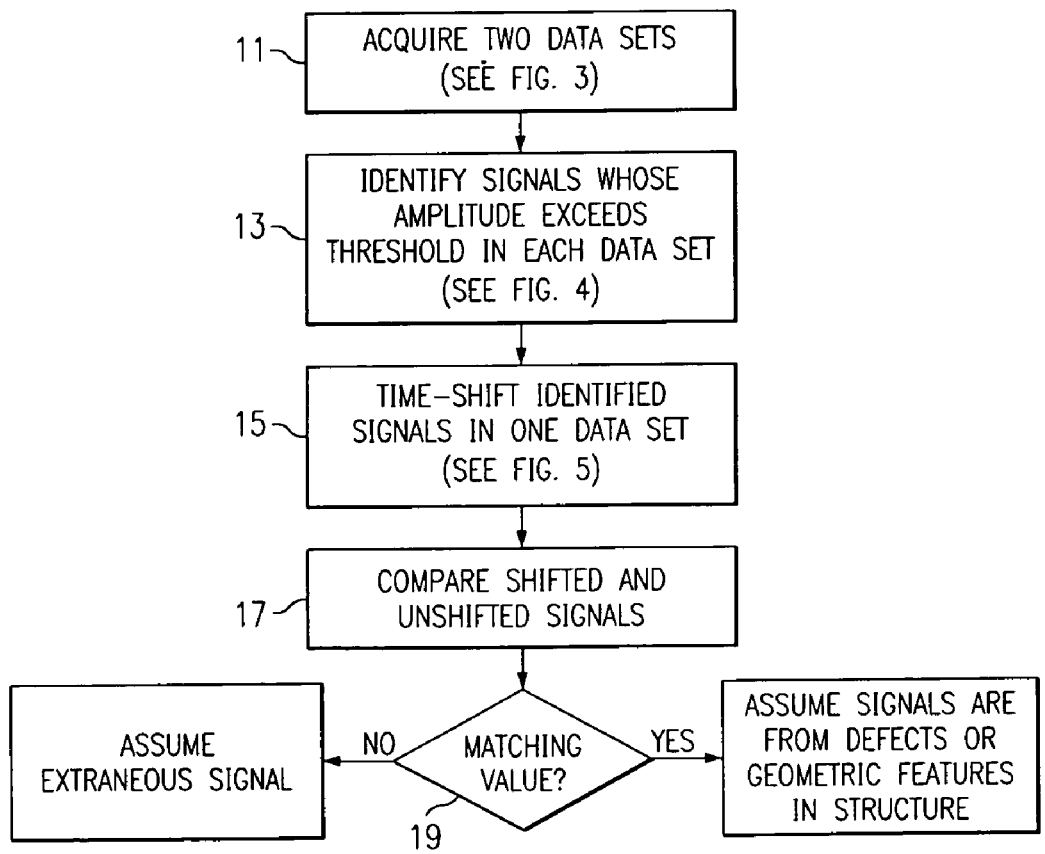
FIG. 2 illustrates the method implemented by the system of FIG. 1.

FIG. 2 illustrates the method implemented by the system of FIG. 1. Essentially, as explained below, the method involves acquiring two sets of data, one set from each probe position 11. Signals whose amplitude is above a pre-determined threshold value are identified from each set. Then, the identified signals in one set are time-shifted, and their shifted occurrence times are compared against those in the other set.

The method may be implemented with either time domain or frequency domain data. The method of FIG. 2 is first described herein in terms of time domain data.

Step 11 is acquiring two sets of guided wave data, each set from a different probe location, with the locations separated by a short distance. For time domain analysis, the two sets of data may be A-scan data, characterized by use of a pulse or tone burst, which is output by a probe and either received by that same probe (pulse echo) or another (pitch catch). The waveform amplitude is plotted versus time.

Figure 3A:
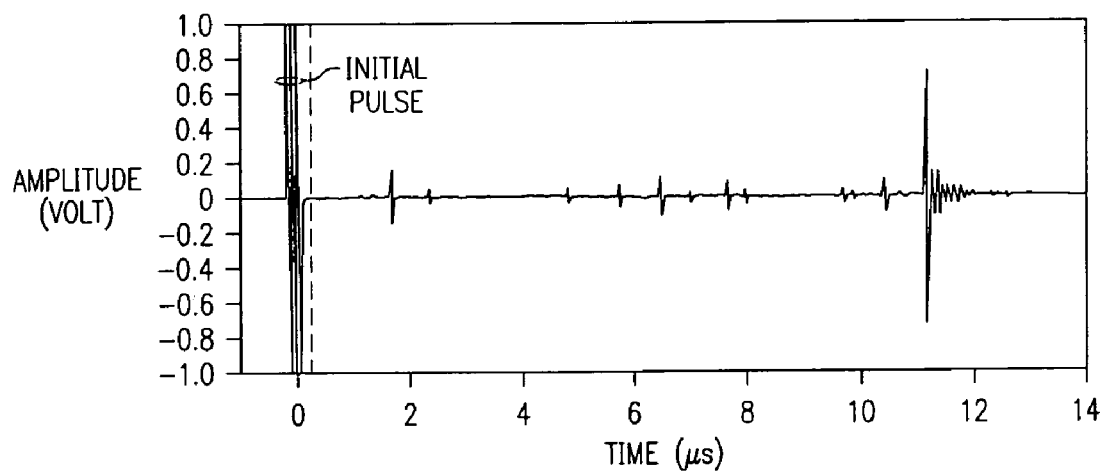
FIG. 3 illustrates the two data sets acquired from the two probe positions described in FIG. 1.
Figure 3B:
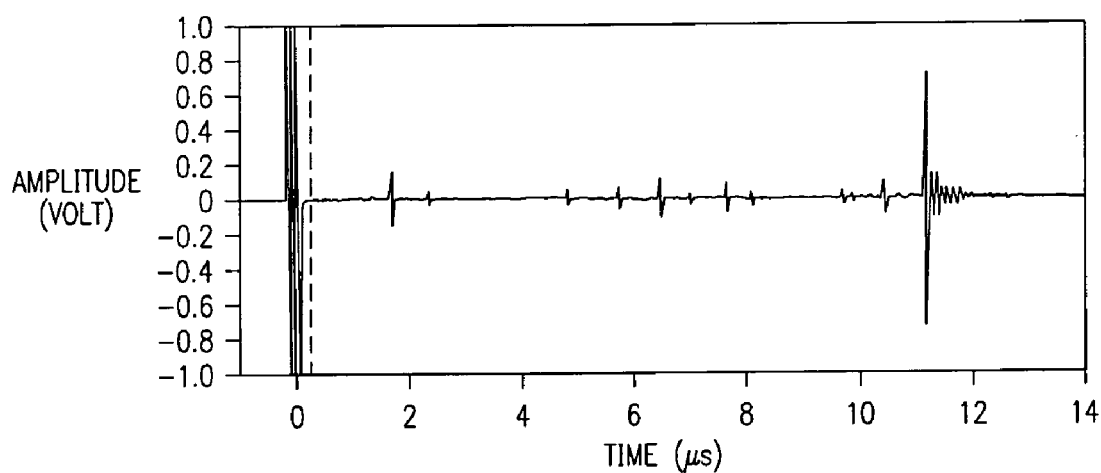

FIGS. 3A and 3B illustrates an example of two sets of A-scan guided wave data from probes 11 placed at two different locations on structure 12. Each set of data is represented by a plot of signal amplitude (volts) against time (milliseconds). The total test time in this case is 14 milliseconds (corresponding to the round-trip time of the longitudinal wave over an approximately 39-meter long pipe), and the range of signal values is within a range of 1 to −1 volts.

Step 13 is identifying signals in both data sets whose amplitude exceeds a certain threshold. The threshold value is chosen to be at least twice the background noise level in the data. The actual threshold value used in the algorithm is determined by the operator based on the desired level of defect detectability (for example 20 percent of a weld signal amplitude).

Various algorithms may be used for implementing Step 13. An example of an algorithm for finding signals whose amplitude exceeds the threshold is begun by first specifying the length of a "gate" to be used. A suitable gate length is one approximately equal to the pulse length of the signal. The signal is then examined within the gate length to determine the maximum signal amplitude, $V_i$, (i=0, 1, 2, . . . numbered consecutively from the first signal identified) within the gate length. If $V_i$ exceeds the threshold, then its occurrence time, $t_i$, is recorded. Otherwise, the data in that gate length is ignored. A number of initial data points from time t= 0, where the initial pulse occurs, may be ignored so as to avoid calling signals caused by the initial pulse.

Successive values of $V_i$ are identified by moving the gate by half gate-length increments, and in each new gate length, determining a maximum value and comparing that value to the threshold. The half-gate length increments are repeated until the end of the data file. The result is a set of maximum amplitude values, each having an associated occurrence time. For each maximum amplitude value, its occurrence time, $t_i$, is compared with the rest of the data point times. Expressed mathematically, each $t_i$ is compared with all other occurrence time values, $t_j$, where j is a value from 1 to n and n is the time of the last point in the data. If $|t_i-t_j|$ is greater than the gate length, then the corresponding amplitude value is chosen for time-shift checking. If $|t_i-t_j|$ is less than or equal to the gate length, this implies more than one amplitude value within a gate and only the corresponding amplitude value within the gate having the maximum amplitude is chosen for time-shift checking. This process of incrementing by half gate lengths and comparing occurrence times is designed to best locate maximum values while avoiding duplicate values. The result is a set of peak signal values, $V_{peak}$, and an associated occurrence time value, within each gate. The peak value occurrence times for the first set of data are referred to herein as $t^1$ times, whereas the occurrence times for the second set of data are referred to herein as $t^2$ times.

Next, for each gate length, in addition to a peak value occurrence time, a median occurrence time value is determined. Within each gate, this is achieved by identifying the first and last time locations at which the signal breaks the threshold. Then, the two values are averaged. The result is two sets of median time values, $t'^1$ and $t'^2$.

Figure 4A:
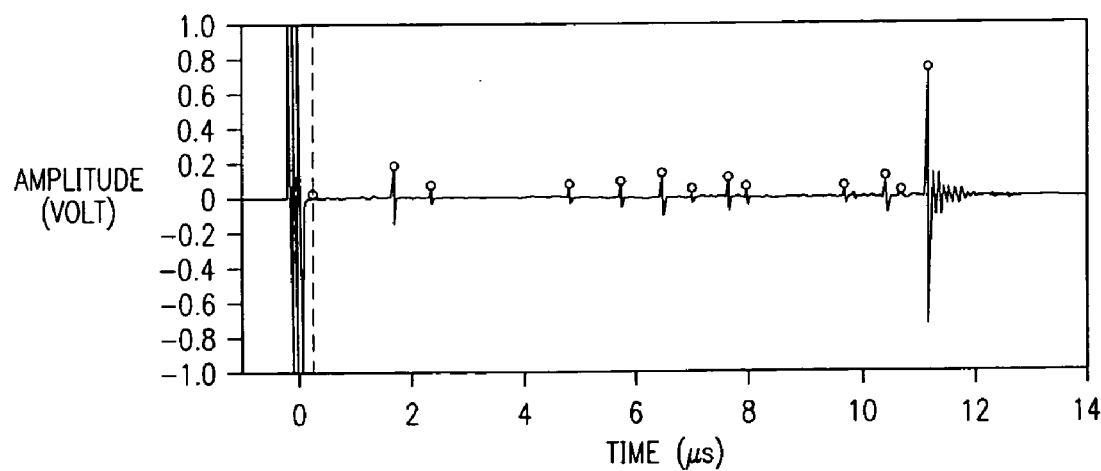
FIG. 4 illustrates the data sets of FIG. 3, with signal amplitude values exceeding a threshold identified.
Figure 4B:
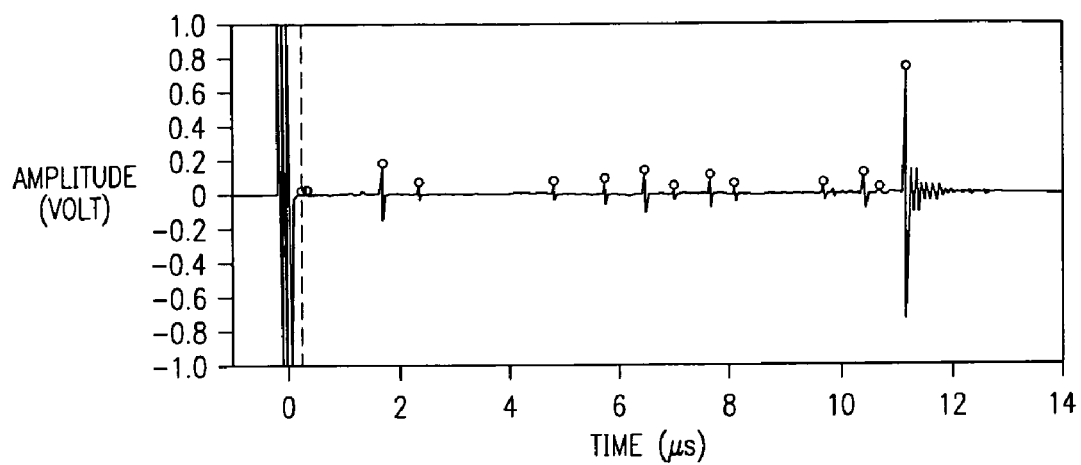

FIG. 4 illustrates the data sets of FIG. 3, with peak data values identified. In the example of FIG. 4, the threshold value was selected to be 0.02 volts of signal amplitude. For the test data of FIG. 4, where the pulse frequency is 64 kHz, a gate length of 3/64 milliseconds could be used.

Step 15 is performed for each of the peak signal values identified in Step 13, in one of the data sets. For each of these signal values, its occurrence time is time-shifted by an amount equal to the roundtrip time of the primary guided wave mode over the distance between the two probe locations. The shifting (addition or subtraction) is performed in such a way that signals from a given reflecting feature, such as a weld or defect, on the side of the structure to which the transmitted wave is directed would occur at the same time in both data sets.

Step 17 and 19 involve reviewing all the selected peak values and locating all peak values in the unshifted data set occurring at the same time as peak values in the shifted data set. Values matching in this manner are interpreted as representing signals from geometric features in the structure or defects. Signals not so matching are interpreted as being caused by extraneous signals and are therefore excluded from further analysis.

An example of an algorithm for implementing Step 17 begins with specifying a time limit within which the signals in both data sets are considered to occur at the same time. Typically, this time limit is set to a value to between 1/2f and 1/f, where f is the operating frequency of the guided wave. Next, time values $t^1$ and $t'^1$ from the data obtained from one probe position are compared to the time values $t^2$ and $t'^2$ from the data obtained from the second probe position. As indicated above in connection with Step 13, each peak data value has four associated time values: $t^1$, $t'^1$, $t^2$, and $t'^2$. If any one of the following four difference values is equal to or less than the specified time limit, then the associated signal value is identified as occurring at the same time in both sets of data: $|t^1-t^2|$, $|t^1-t'^2|$, $|t'^1-t^2|$, and $|t'^1-t'^2|$. In other words, the signal values are "matching". The matching signal values are considered to represent defects or geometric features in the structure being tested. If none of the above four values is equal to or less than the specified time limit, then the signal value is not considered to occur at the same time in both sets of data, and is therefore ignored.

Figure 5A:
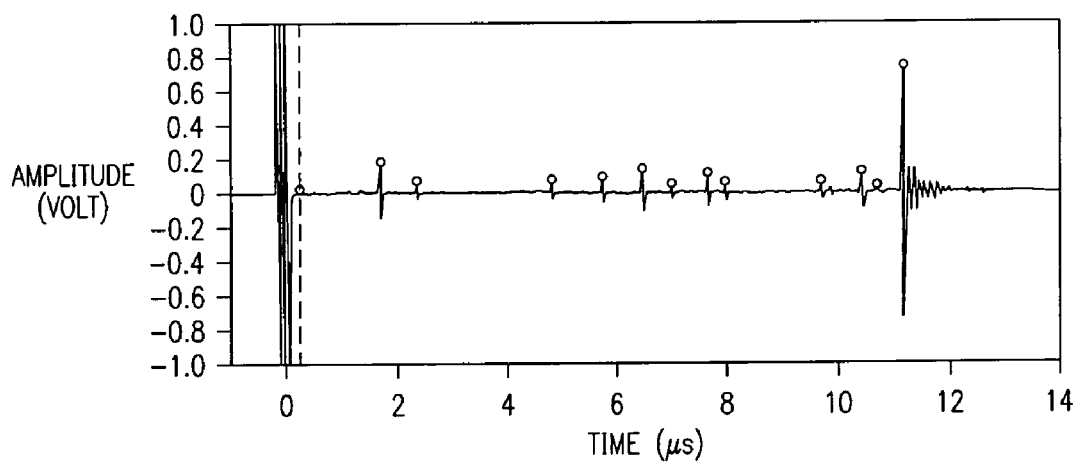
FIG. 5 illustrates the identified signal values of FIG. 4, with further identification of signal values in the second set that are within a specified time limit of signal values in the first set.
Figure 5B:
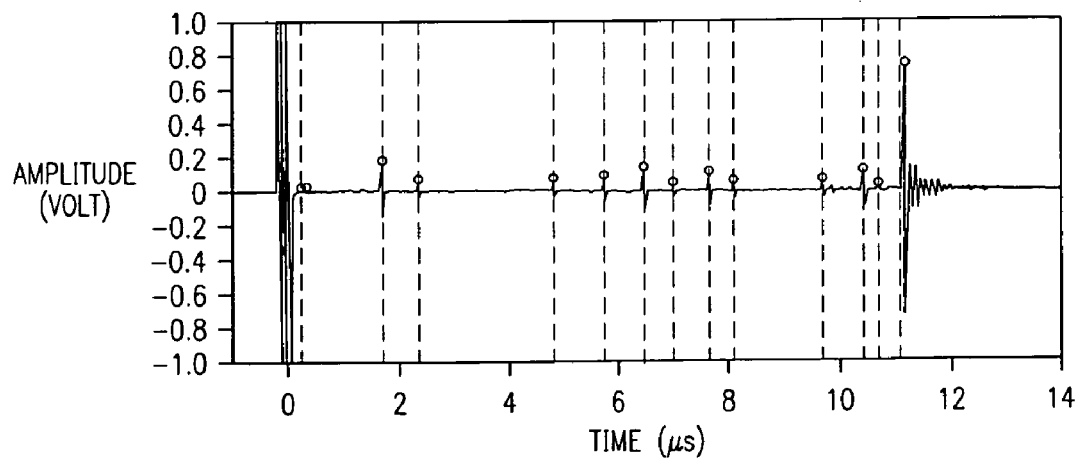

FIG. 5 illustrates the same signals as FIGS. 3 and 4, but with identification of matching signal values, that is, the signal values from one set that are within the specified time limit of signal values from the other data set. These signals are identified as "real" signals, which indicate defects and geometric features in the structure (in this case a pipeline).

Because of wave attenuation, signals from the same defects or geometric features decrease in amplitude with increasing transit-time (or distance to the probe position). The constant threshold values used in the method described in FIG. 2 mean that the level of defect detectability decreases with increasing time in the data. A constant level of defect detectability can be maintained by either compensating the attenuation effect on the data or by applying the attenuation to the threshold value.

Frequency Domain Data Analysis

For frequency domain data analysis, A-scan data may be converted to spectrogram data. A method for this type of analysis is described in the following article: H. Kwun, K. A. Bartels, and C. Dynes, "Dispersion of Longitudinal Waves Propagating in Liquid-Filled Cylindrical Shells," J. Acouset. Soc. Am. 105, pp. 2601–2611, 1999. To preserve spatial resolution, the window length used for spectrogram analysis is kept as short as possible but sufficiently long so that dispersion properties of the waves are observable.

The spectral amplitude at several frequencies is summed. Using the summed spectral amplitude data, the process described above for time domain data is performed. For identifying signals exceeding a threshold (Step 13), the process is performed using maximum spectral amplitudes. An additional step of checking data values on either side of identified maximum values to discard non peak values may be performed. Signals that occur at the same time in both sets of data are identified. The identified signals are then converted back to A-scan data.

Other Embodiments

Although the present invention has been described in detail, it should be understood that various changes, substitutions, and alterations can be made hereto without departing from the spirit and scope of the invention as defined by the appended claims.

What is claimed is:

1. A method of using long range guided wave inspection techniques to detect geometric irregularities in a cylindrical shell structure, comprising the steps of:
   generating a first long range wave from a first probe at a first probe position along the cylindrical shell, wherein the first long range wave travels substantially in one direction from the probe along a length of the structure;
   acquiring a first data set representing reflection signals reflected from an irregularity to the first probe;
   generating a second long range wave from a second probe at a second probe position along the cylindrical shell having a known separation from the first probe position, wherein the second long range wave travels in the same direction relative to the first long range wave;
   acquiring a second data set representing reflection signals reflected from the irregularity to the second probe position;
   wherein the first probe and the second probe are external to the structure;
   wherein the first long range wave and the second long range wave are substantially of a single wave mode of a fixed order, both propagated in a single direction relative to each other;
   identifying peak signal values in the first data set and in the second data set, thereby obtaining a first set of peak signal values and a second set of peak signal values; associating each peak signal value with an occurrence time;
   time-shifting one set of peak signal values by an amount equal to the roundtrip time of the first long range wave over the distance between the first probe and the second probe;
   determining a coincidence in time of values in the shifted set of peak signal values and values in the unshifted set of peak signal values; and
   interpreting coincident values as corresponding to an irregularity in the structure.

2. The method of claim 1, wherein the first data set and the second data set are in the time domain.

3. The method of claim 2, wherein the first data set and the second data set represent A-scan data.

4. The method of claim 1, wherein the first data set and the second data set are in the frequency domain.

5. The method of claim 4, further comprising the step of converting the first data set and the second data set to time domain data before performing the identifying step.

6. The method of claim 1, wherein the identifying step is performed by defining a gate length and selecting a maximum signal value within each of a series of gate lengths.

7. The method of claim 1, wherein the determining step is performed by defining a time limit within which both a value in the shifted set of peak signal values and a value in the unshifted set of peak signal values must occur.

8. The method of claim 1, wherein the occurrence times correspond to peak signal values.

9. The method of claim 1, wherein the occurrence times are determined by the median time during which data values exceed a threshold.

10. The method of claim 1, wherein the probes are suitable for magnetostrictive testing.

11. The method of claim 1, wherein the probes are suitable for Lamb wave testing.

12. A method of using long range guided wave inspection techniques to detect geometric irregularities in a conduit, comprising the steps of:
   generating a first long range wave from a first probe at a first probe position along the conduit, wherein the first long range wave travels substantially in one direction from the first probe along a length of the conduit;
   acquiring a first data set representing reflection signals reflected from an irregularity in the conduit to the first probe;
   generating a second long range wave from a second probe at a second probe position along the conduit having a known separation from the first probe position, wherein the second long range wave travels in the same direction relative to the first long range wave;
   acquiring a second data set representing reflection signals reflected from the irregularity in the conduit to the second probe position;
   wherein the first probe and the second probe are external to the conduit;
   wherein the first long range wave and the second long range wave are substantially of a single wave mode of a fixed order, propagated in a single direction relative to each other;
   identifying peak signal values in the first data set and in the second data set, thereby obtaining a first set of peak signal values and a second set of peak signal values; associating each peak signal value with an occurrence time;
   time-shifting one set of peak signal values by an amount equal to the roundtrip time of the first long range wave over the distance between the first probe and the second probe;
   determining a coincidence in time of values in the shifted set of peak signal values and values in the unshifted set of peak signal values; and
   interpreting coincident values as corresponding to an irregularity in the conduit.

13. The method of claim 12, wherein the first data set and the second data set are in the time domain.

14. The method of claim 13, wherein the first data set and the second data set represent A-scan data.

15. The method of claim 12, wherein the first data set and the second data set are in the frequency domain.

16. The method of claim 15, further comprising the step of converting the first data set and the second data set to time domain data before performing the identifying step.

17. The method of claim 12, wherein the identifying step is performed by defining a gate length and-selecting a maximum signal value within each of a series of gate lengths.

18. The method of claim 12, wherein the determining step is performed by defining a time limit within which both a value in the shifted set of peak signal values and a value in the unshifted set of peak signal values must occur.

19. The method of claim 12, wherein the occurrence times correspond to peak signal values.

20. The method of claim 12, wherein the occurrence times are determined by the median time during which data values exceed a threshold.

21. The method of claim 12, wherein the probes are suitable for magnetostrictive testing.

22. The method of claim 12, wherein the probes surround a section of the conduit.

* * * * *